United States Patent [19]

Carroll

[11] 4,223,040

[45] Sep. 16, 1980

[54] LAURIC ACID FOR THE PREVENTION AND TREATMENT OF MYCOBACTERIAL DISEASES

[76] Inventor: John M. Carroll, 1421 Royal St., Kissimmee, Fla. 32741

[21] Appl. No.: 527,359

[22] Filed: Nov. 26, 1974

Related U.S. Application Data

[63] Continuation-in-part of Ser. No. 230,115, Feb. 28, 1972, abandoned, which is a continuation of Ser. No. 844,162, Jul. 23, 1969, abandoned.

[51] Int. Cl.$^2$ ............................................. A61K 31/20
[52] U.S. Cl. .................................................... 424/318
[58] Field of Search ........................................ 424/318

[56] References Cited

PUBLICATIONS

Katsura et al., Chem. Abst. vol. 43 (1949) 5906b.
Carroll, "In Vitro and in Vivo Studies with Mycobacterium Paratuberculosis" (1965).

Primary Examiner—Allen J. Robinson
Attorney, Agent, or Firm—Brumbaugh, Graves, Donohue & Raymond

[57] ABSTRACT

A method for the prevention and treatment of mycobacteriosis in mammalian tissue which comprises administering an effective dose of lauric acid.

4 Claims, No Drawings

LAURIC ACID FOR THE PREVENTION AND TREATMENT OF MYCOBACTERIAL DISEASES

This application is a continuation-in-part of my co-pending application Ser. No. 230,115, filed Feb. 28, 1972, now abandoned, which in turn is a continuation of my application Ser. No. 844,162, filed July 23, 1969, now abandoned.

The present invention relates to the use of lauric acid as an active mycobacteriostatic agent to prevent and treat infection by *M. tuberculosis* and other pathogenic mycobacteria in mammalian tissue.

Leprosy, tuberculosis and paratuberculosis are the most prominent diseases caused by pathogenic species of the genus Mycobacterium. Leprosy is a chronic, infectious ailment caused by *M. Leprae*, an organism which has not as yet been cultivated in vitro or successfully transmitted to experimental animals. *M. tuberculosis* was first isolated by the German bacteriologist Robert Koch in 1882 as the causitive agent of the infectious disease tuberculosis. Thousands of compounds of natural and synthetic origins were thereafter tested for their efficacy as mycobacteriostatic and mycobactericidal agents. While a large number of compounds have been found active in vivo at low concentrations against mycobacterial infection, the number of compounds showing demonstrated clinical usefulness is extremely small.

For instance, streptomycin is a known clinically effective mycobacteriostatic agent for the treatment of various forms of tuberculosis. However, streptomycin has several disadvantages such as poor absorption when administered orally and, upon prolonged use at high dosage levels, it may cause vestibular damage. Other natural antibiotics which demonstrate antibacterial activity toward mycobacteria all have limited usefulness due to some serious drawback or another, such as lack of stability, hypertoxicity, bacterial resistance and risk of vestibular damage. Of the synthetic agents that have been developed, most are impracticable due to hypertoxicity and many of those which have acceptable toxicity levels demonstrate weak antibacterial effects. Furthermore, those compounds which have been found to demonstrate clinical usefulness as mycobacteriostats or mycobactericides or both have been found effective for only certain forms of mycobacterial disease and only when used in combination with other therapeutic agents together with bed rest and, in some cases, surgery.

Paratuberculosis is a chronic, infectious disease primarily of cattle and sheep and occasionally of other animals which is caused by *M. paratuberculosis*. Paratuberculosis, which is not pathogenic for humans, is characterized by recurrent diarrhea, progressive emaciation and thickening and corrugation of the intestinal mucosa followed by death. There are known preventative or therapeutic agents for this disease.

Furthermore, there is not at the present time any composition, natural or synthetic, which is generally effective for preventing and destroying Mycobacterium species in mammalian tissue.

Accordingly, it is an object of the present invention to provide a preventive and therapeutic composition and a method for inhibiting the growth of all species of Mycobacterium in mammalian tissue.

It is a further object of this invention to provide a mycobacteriostatic agent which has a low toxicity and which may be administered orally or by parenteral injection.

It has now been found that lauric acid is an effective mycobacteriostatic agent against bacteria of the genus Mycobacterium. In vitro tests have shown that concentrations of lauric acid ranging from 0.02 mg/ml to 0.5 mg/ml prevented the growth of two strains of *M. tuberculosis*, two strains of *M. paratuberculosis* and one strain of *M. phei*. In vivo tests using black mice have demonstrated that lauric acid at a level of 4%–8% in the feed prevented the death of the mice when inoculated intraperitoneally with a lethal dose of *M. paratuberculosis*. Guinea pigs were protected from and cured of tuberculosis (*M. tuberculosis*) when regularly given lauric acid in their dry feed in a concentration of 4%. In addition, cows with severe continuous symptoms of clinical paratuberculosis were free of all symptoms and of normal strength and appearance within 21 days after receiving effective amounts of lauric acid in their daily feed.

It is believed that lauric acid interferes with the enzyme systems of the genus Mycobacterium thereby inhibiting the growth of these organisms. The exact biochemical explanation of this phenomenon is, however, unknown.

In accordance with the method of this invention, lauric acid is brought into effective contact with the mycobacterium by ingestion or parenteral injection in the form of a pharmaceutical preparation comprising an active dose of lauric acid. These preparations contain between 10 and 30 percent by weight for preparations to be injected. For preparations intended for oral consumption, about 4%–8% is added to the daily food consumption, while tablets may contain as much as 90% lauric acid. Tablet form lauric acid has limited particularity due to the large quantities of acid required to constitute an effective dose.

For oral administration, the lauric acid may be administered in several different ways. If feasible, it may be added to the normal daily diet of the mammal. If a solid pharmaceutical preparation is desirable, the lauric acid may be mixed with a solid pulverulent carrier, for example, lactose, sacchrose, sorbitol, mannitol, starch, such as potato starch, corn starch, amylopectin, laminaria powder or a citrus pulp powder, cellulose derivatives or gelatin. The preparation may also include a lubricant such as magnesium or calcium stearate or a Carbowax or other polyethylene glycolwax, the final mixture being compressed to form tablets. When coated tablets are required, the cores may be coated with a concentrated sugar solution which may contain, for example, gum arabic, talcum and titanium dioxide. Alternatively, the tablets may be coated with a lacquer dissolved in a volatile organic solvent or a mixture of organic solvents. Dyestuffs may be added to these coatings for distinction between tablets containing different contents of the active acid ingredient. For the preparation of soft gelatin capsules (pearl-shaped, closed capsules) consisting of gelatin and, for example, glycerol and similar closed capsules, the active substance may be admixed with a vegetable oil. Hard gelatin capsules may contain granulates of the active substance in combination with solid pulverulent carriers such as lactose, sacchrose, mannitol, starches, for example, potato starch, corn starch or amylopectin, cellulose derivatives or gelatin.

Liquid preparations for oral administration may be in the form of syrups or suspensions, for example preparations containing from about 20 to 90 percent by weight of lauric acid, sugar and a mixture of ethanol, water and glycerol, propylene glycol, and in addition, flavoring agents, saccharin and carboxymethylcellulose and a thickening agent.

For administration by means of parenteral injection, the lauric acid must be incorporated with a liquid carrier in which it is either soluble or in which the lauric acid crystals are of a size small enough to produce a suspension or dispersion in the carrier suitable for inoculation. Since most carriers in which lauric acid is soluble demonstrate hypertoxicity, such as ethanol, ether and propylene glycol, other less toxic, non-solvent carriers are preferred.

For lauric acid to be effectively injected in a liquid carrier wherein the acid is insoluble, such as water, the lauric acid particles must be of a size ranging between 0.01 and 5 microns. An injectable aqueous dispersion of lauric acid having a suitable particle size within this range may be prepared in the following manner: (1) a mixture of lauric acid and an aqueous medium, preferably containing a volatile dispersing agent or a surfactant is formed, and (2) the mixture is subjected to intense agitation under conditions which provide lauric acid crystals within the prescribed range. A more detailed discussion on the preparation of injectable lauric acid may be found in my copending application Ser. No. 844,193, filed July 23, 1969, now U.S. Pat. No. 3,658,970.

The dosage amount depends upon the ecology of the region, the condition of the inflicted mammal, the manner of administration and the desired preventative or therapeutic effect. Generally the daily dosage will vary from 1 g to about 10 g of lauric acid per kilo of body weight of the mammal based upon 4% lauric acid in a dry feed.

The toxicity of lauric acid to mammals is very low. Lauric acid may be used in comparatively large doses and over extended periods of time with no undesirable side effects.

In order to determine the efficacy of lauric acid for destroying and inhibiting the growth of mycobacteria in mammalian tissue, several experiments were performed with black mice, guinea pigs and cows.

In in vivo experiments with black mice, ten C57 black mice were inoculated intraperitoneally with 0.2 ml of a suspension of a *M. paratuberculosis* second transfer culture (30% light transmission with a 640 mu filter, Coleman Junior Spectrophotometer, Coleman Instrument, Inc., Maywood, Ill.). Five of these mice received only a commercial animal feed (Lab Chow, Ralston-Purina, Davenport, Iowa) during the experiment. The remaining five mice were prefed 4% lauric acid in their dry feed continuously during the 14 day period before infection and were continued on this level of lauric acid after inoculation.

The five untreated mice all died within sixty-eight days. After the same time period, the mice that were on lauric acid were all alive, healthy and approximately 30% larger and heavier than those not given lauric acid. Kidneys, lungs, livers, spleens, pancreata and visible lymph nodes were collected from the five untreated mice and from the fice mice on 4% lauric acid, which were killed for comparative purposes. The majority of tissues from each of the five untreated black mice were bacteriologically and histopathologically positive for acid-fast organisms. On the other hand, the tissues from the treated mice were negative. Histopathologically, the tissues from the untreated mice showed aggregates of macrophages, early granuloma formation and early tubercle-like lesions. The tissues of the treated mice did not show any significant lesions.

These mice experiments specifically show that the presence of high levels of lauric acid in the diet will prevent the growth of *M. paratuberculosis* in mammalian tissue.

A lyophilized culture of *M. tuberculosis* was used for the guinea pig experiments. In a preliminary test, two untreated guinea pigs were inoculated intraperitoneally with *M. tuberculosis* by cultures and direct tissue smears was conclusive that this culture was virulent. The addition of 0.5 mg/ml of a lauric acid suspension in a modified Long's medium for *M. tuberculosis* completely inhibited the growth of this culture.

The modified Long's media used in these experiments had the following composition:

| | | |
|---|---|---|
| L. asparagine | 5.0 | g/l |
| Potassium Acid Phosphate (monobasic) | 3.0 | g/l |
| Ammonium Citrate | 5.0 | g/l |
| Magnesium Sulfate | 1.0 | g/l |
| Sodium Chloride | 2.0 | g/l |
| Sodium Carbonate (anhydrous) | 3.0 | g/l |
| Fe Ammonium Citrate | .05 | g/l |
| Glycerol | 50.0 | g/l |
| Casamino Acids | 30.0 | g/l |
| Distilled Water | 1 | liter |

Solid media used contained an added 20.0 g/l agar.

In these in vivo tests involving guinea pigs, the animals were separated into five groups. Group I (negative control) received a commercial animal feed (Lab Chow, Ralston-Purina, Davenport, Iowa) cabbage and water. Group II (negative, medicated control) received the commercial animal feed with 4% lauric acid, cabbage and water. Group III was prefed the commercial animal feed with 4% lauric acid, cabbage and water for 21 days, after which time the guiena pigs in Group III were inoculated intraperitoneally with 0.1 mg of *M. tuberculosis* using known procedures. Group IV (positive control) received only the commercial animal feed, cabbage and water during the experiment and were similarly inoculated intraperitoneally with 0.1 mg of *M. tuberculosis* after 21 days. Group V-A and V-B received the commercial animal feed, cabbage and water until 30 days after infection by similar inoculation, and at which time two guinea pigs designated V-A1 and V-A2 were euthanized for evidence of tuberculosis. Mucoid material was aspirated from the pharyngeal region of the remaining guinea pigs designated Group V-B for bacteriological recovery and direct smears. Group V-B was then fed 4% lauric acid in their dry feed.

The aspirated pharyngeal material (0.25 to 0.5 ml) was suspended in 5 ml quantities of a 1:20 dilution of commercial Clorox and sterile water. These tubes were shaken for 2–3 minutes with a Vortex mixer to oxidize, then centrifuged at 6000 r.p.m. in an angle-head centrifuge for 10 minutes. The supernatent Clorox solution was then decanted and the sediment resuspended in 0.34% Benzalkonium chloride solution (Zephiran) (6 ml/100-$H_2O$ of 1-750 aqueous solution). After resuspending by Vortex shaking and recentrifuging, the sediment was washed twice in sterile physiologic saline solution (PSS) by sedimentation and high speed centrifugation. The last PSS sediment was resuspended in 0.5 ml quantities of sterile PSS and smears prepared for acid-fast staining. The remaining sediment was then suspended in 5 ml quantities of modified Long's medium and cultured.

The tissues collected from all guinea pigs that died or were euthanized consisted of lung, liver, spleen, kidney, pancreas, adrenals and any lymph nodes that could be found during necropsy. The tissues were first individually inoculated aseptically into tubes containing the modified Long's medium. The tissues were then combined for a composite bacteriological recovery of *M. tuberculosis*. Identical tissues were used to make direct smears and for histopathological examination.

The composite tissues were treated as follows: Small pieces of each tissue collected were transferred to a sterile mortar with sterile alundum and ground with a pestle. The ground material was suspended in 10 cc. quantities of sodium hypochlorite solution (76.0 ml commercial bleach/4000 ml sterile water). The supernate from ground material was aseptically transferred to sterile tubes and centrifuged lightly (1000 r.p.m. 3 min.) to remove heavier particles and sand. The supernate from these tubes was then transferred to sterile tubes and centrifuged at 6000 r.p.m. for 10 minutes until optically clear and the supernate discarded. The sediment was resuspended in 0.34% Zephiran solution and shaken for 3 to 5 minutes with a Vortex mixer. The tubes were then centrifuged at high speed for 10 minutes and the supernate discarded. After 2 washings in sterile physiological solution, the sediment was then suspended in 5 ml quantities of modified Long's broth media and incubated at 37° C. for 14 days, when subcultures were prepared on modified Long's solid media. Both broth and solid cultures were incubated at 37° C. and smears from these cultures prepared at 10-12 day intervals beginning at five weeks after culture inoculations and continuing for a total of five examinations.

Under acid-fast staining (Ziehl-Neelsen with Aerosol OT as a surface depressant), acid-fast rods could be demonstrated when present.

Groups I, II, III and V-B did not show any clinical symptoms when euthanized 82 days after infection and Groups V-A and V-B showed loss of weight and rough hair coats at 30 days after infection. Group IV showed emaciation, diminished growth, rough hair coats and alopecia at time of death from the 62nd through the 75th day post-inoculation.

Groups I, II, III and V-B did not show any gross necropsy lesions and lymph nodes could not be found. Guinea pigs V-A1 and V-A2 showed loss of internal adipose tissue and enlarged lymph nodes. Group IV showed complete loss of body fat, atrophy of the spleen, enlarged lymph nodes and enlarged adrenals with some showing hemorrhage.

Tissues were collected from all 5 groups of guinea pigs, processed for histopathological study and stained using the Ziehl-Neelsen method. The tissues were prepared to demonstrate the presence or absence of acid-fast organisms. However, all observable histopathological lesions under Ziehl-Neelsen staining were recorded. Since the acid-fast stain was used, only the most obvious lesions were observed.

The tissues from all guinea pigs in Groups I, II, III and V-B were negative for acid-fast organisms. The majority of tissues from each guinea pig in Group IV and guinea pigs V-A1 and V-A2 were positive for acid-fast organisms.

Groups I and II showed lymphoid foci in the lungs, fatty infiltration of livers and hemosiderin in the spleen.

Group III showed hyperplasia of the splenic corpuscles and excessive hyperplastic lymphoid foci in the lungs.

In Group IV, the lungs showed microhemorrhage, large alveolar aggregates of lymphocytes, large mononuclear cells, polymorphs and Langhan's giant cells. There were perivascular infiltrated large mononuclear cells, lymphocytes and polymorphs. The lungs also showed congestion with focal emphysema and collapse. The spleen showed loss of white pulp (lymphoid depletion) and infiltrated large mononuclear cells and polymorphs. The lymph nodes showed lymphoid hyperplasia, infiltrated large mononuclear cells, Langhan's giant cells and early granulomas. The livers showed infiltrated lymphocytes and polymorphs and focal aggregates of polymorphs with innumerable acid-fast organisms (early tubercle formation). The adrenals showed congestion, microhemorrhage, infiltrated large mononuclear cells, lymphocytes, polymorphs and edema.

In Group V, the guinea pigs designated V-A1 and V-A2 showed alveolar aggregates of lymphocytes, large mononuclear cells, polymorphs and a Langhan's giant cell. The lymph nodes showed lymphoid hyperplasia and infiltrated large mononuclear cells and polymorphs. The adrenal and liver showed infiltrated polymorphs and lymphocytes.

Group V-B showed lymphoid hyperplasia and infiltrated polymorphs in the spleen. The lungs showed excessive hyperplastic lymphoid foci and focal fibrosis. The livers and adrenals showed fatty infiltration.

Bacteriological results in general corresponded with the pathological findings. Tissues from Groups I, II, III and V-B were bacteriologically negative for isolation of *M. tuberculosis*. Cultures of the tissues from Group IV and guinea pigs V-A1 and A2 resulted in isolation of *M. tuberculosis*.

TABLE I

| | CONTROLS | | INFECETED GUINEA PIGS | | | |
|---|---|---|---|---|---|---|
| | | | Prefed 4% | | Normal Feed | Feed w/4% Lauric |
| Group No. | Normal Feed I | Normal Feed w/ 4% Lauric Acid II | Lauric Acid and Cont. III | Normal Feed Only IV | 30 days post inf. V-A | Acid Start 30 days post inf. V-B |
| No. of G.P.'s | 6 | 6 | 7 | 8 | 2 | 6 |
| Smears Phary. Mucos Cult. | X | X | X | X | X | +(6)* |
| Pharyl Mucous Direct. | X | X | X | X | X | +(6) |
| Tiss. Smears | — | — | — | + | + | — |

TABLE I-continued

|  |  | CONTROLS | | INFECETED GUINEA PIGS | | | |
|---|---|---|---|---|---|---|---|
|  |  |  |  | Prefed 4% |  | Normal Feed | Feed w/4% Lauric |
|  |  | Normal Feed | Normal Feed w/ 4% Lauric Acid | Lauric Acid and Cont. | Normal Feed Only | 30 days post inf. | Acid Start 30 days post inf. |
| Group No. | | I | II | III | IV | V-A | V-B |
| Acid- | Liv. | — | — | — | +(5/8-8/8)* | +(2)* | — |
| Fast | Lg. | — | — | — | +(4/8-8/8) | +(2) | — |
| smears | Kid. | — | — | — | +(2/8-7/8) | +(2) | — |
| from | Sp. | — | — | — | +(5/8-8/8) | +(2) | — |
| culture | Pan. | — | — | — | +(7/8-8/8) | +(2) | — |
|  | Adr. | — | — | — | +(6/8-8/8) | +(2) | — |
|  | L.G. | NGV | NGV | NGV | +(3/8-8/8) | +(2) | NGV |
|  | C.T. | — | — | — | +(3/8-8/8) | +(2) | — |

Stain = Ziehl-Neelsen w/Tergitol OT + 3% HCL Alcohol.
counter stain = Meth. Blue.
— = Negative acid-fast
+ = Positive acid-fast
X = Not made
C.T. = Composite tissues.
NGV = Not grossly visible.
*(Pos./Total Animals).

The results of the guinea pig experiments as reported in Table I coupled with the results of the in vitro testing and mice experiments indicate the inhibiting effect of lauric acid on the growth of M. tuberculosis and M. paratuberculosis and demonstrate the efficacy of lauric acid in preventing tuberculosis in mammalian tissue.

In in vivo experiments with cows, 10 registered Jersey cows with clinical paratuberculosis were given lauric acid mixed with their protein supplement feed in an amount equal to 1 gram per kilogram per day. The cows showed cessation of the symptoms of paratuberculosis and improvement in physical condition within 21 days. Four of these cows died from causes other than paratuberculosis before the conclusion of the tests. The six remaining cows, after receiving lauric acid in their feed for intervals varying from 48 days to 122 days, had corresponding survival times of 157 days to 332 days. The feces of these six cows were negative for *Mycobacterium paratuberculosis* within 41 to 112 days. Details of the tests and the results therefrom are described below.

The experiments were conducted with a herd of Jersey cows consisting of about 500 animals on 250 acres of improved pasture in Florida. This herd had approximately 330 lactating cows during a 12 month period. The cattle were maintained on good permanent pasture during the entire year, with hay supplements required only rarely. The cattle were also fed a high protein supplement at the rate of 25 pounds per cow per day. This feed consisting of processed citrus pulp, fortified with high protein feed, salt, minerals and vitamins. The cattle were maintained on a regular worming schedule. In the herd in question, the annual death loss over a 15 year period from acute paratuberculosis was approximately 5%. Seventeen of 24 unbred heifers from the best breeding stock reacted strongly to intradermal Johnin. In accordance with past experience with the herd, the cows which manifested clinical tuberculosis were those which were high milk producers, and over 95% of those which evidenced clinical symptoms of paratuberculosis died with 21 days after the onset of the symptoms, although a few would live as long as 42 days.

At the time these tests commenced, ten cows from the herd evidenced severe symptoms of clinical paratuberculosis and were expected to die within 21 days. These cows had continuous fetid diarrhea, rapid loss of weight, loss of milk production, rough dull dry hair coats, slightly humped backs and general weakness but with good appetite. The cows were wormed with Tramisol, a proprietary worming medication sold by Cyanamid and were treated therapeutically with various combinations of triple sulfa, (a mixture of sulfanilamide, sulfathiazole and sulfamethazine (Anchor)), penicillin-dihydrostreptomycin (Pfizer), Furacin (Eaton), Terramycin (Pfizer), Flucort (Syntex) and injectable iron.

In addition, each cow was given 0.2 ml of intradermal Johnin, U.S.D.A., within the center of a 7 cm. sq. shaved area in the mid-cervical region. Rectally collected feces were tested for *M. paratuberculosis*. The ten cows did not respond to the preliminary treatments for diarrhea within three days, were positive to the intradermal Johnin within three days, and had acid fast organisms in direct fecal smears. The presence of *M. paratuberculosis* organisms was determined by the standard test for isolation of *M. paratuberculosis* set forth on pages 20 and 21 of the manual entitled "Mycobacteriology," published by Diagnostic Services, Animal Health Division, National Animal Disease Laboratory, Ames, Iowa, (1969). The mycobactin used in the test was obtained from National Animal Disease Laboratory, Ames, Iowa.

These cows were given lauric acid in their protein supplement equal to 1 gram per kilogram of body weight per day. Fecal samples were collected for testing at regular intervals. The feeding of lauric acid continued for from 48 to 122 days.

The ten cows given lauric acid had normal feces, gained weight, had smooth, glossy hair coats, straight backs and normal physical strength within 21 days after commencing the dosage with lauric acid. Of the ten cows, four died for reasons unrelated to the paratuberculosis infection. The following table summarizes the data relating to these four animals:

TABLE II

| Cow No. | Age Yrs. | Symptoms of PTB* | Response to Antibiotics | Johnin Test | Fecal Smears | Culture for PTB** | No. days on lauric acid | Response to lauric acid | Cause of death |
|---|---|---|---|---|---|---|---|---|---|
| 47 | 6 | + | – | – | + | – | 32 | + | pneumonia |

TABLE II-continued

| Cow No. | Age Yrs. | Symptoms of PTB* | Response to Antibiotics | Johnin Test | Fecal Smears | Culture for PTB** | No. days on lauric acid | Response to lauric acid | Cause of death |
|---|---|---|---|---|---|---|---|---|---|
| 148 | 7 | + | − | + | + | + | 43 | + | pneumonia |
| 352 | 5 | + | − | + | + | + | 51 | + | hypomagnesemia |
| 5 | 6 | + | − | + | + | + | 62 | + | hypomagnesemia |

*Paratuberculosis
**Test on pages 20 and 21 of the manual entitled "Mycobacteriology", published by Diagnostic Services, Animal Health Division, National Animal Disease Laboratory, Ames, Iowa, (1969)

Two of the cows died with severe symptoms of pneumonia, which apparently was brought about by a change of pasture and extreme weather conditions which fluctuated between 84° F. and 26° F. together with driving cold rain and winds of over 70 miles per hour. In addition, two cows died with symptoms of hypomagnesemia (grass tetny). At the time of death of these four cows, they had been receiving lauric acid for 32, 43, 51 and 62 days respectively, and in each case the cows were in normal physical condition with no clinical symptoms of paratuberculosis.

The balance of the cows in this test, six in number, were given lauric acid in their feed for from 48 days to 122 days, after which their diet was returned to normal. Fecal samples from the six cows became negative for paratuberculosis organisms after from 41 to 112 days. Data for these six cows are represented in the following table:

TABLE III

| Cow No. | Age Yrs. | Symptoms of PTB* | Response to Antibiotics | Johnin Test | Fecal Smears | Culture for PTB** | No. days on lauric acid | Response to lauric acid | Negative feces days | No. days lived |
|---|---|---|---|---|---|---|---|---|---|---|
| 209 | 8 | + | − | + | + | + | 122 | + | within 84 | 332 |
| 321 | 6 | + | − | + | + | + | 107 | + | within 69 | 247 |
| 137 | 6 | + | − | + | + | + | 102 | + | within 41 | 161[1] |
| 208 | 4 | + | − | + | + | + | 69 | + | within 112 | 239 |
| 112 | 5 | + | − | + | + | + | 48 | + | within 62 | 157 |
| 43 | 6 | + | − | + | + | + | 48 | + | within 62 | 157+[2] |

[1] died with severe symptoms of pneumonia, was in normal physical condition without clinical symptoms of paratuberculosis
[2] no record of death, thought to be in dry herd
*Paratuberculosis
**Test on pages 20 and 21 of the manual entitled "Mycobacteriology", published by Diagnostic Services, Animal Health Division, National Animal Disease Laboratory, Ames, Iowa, (1969)

The cows were exposed to a bull at signs of estrus and cow No. 209 gave birth to a live calf 316 days after the start of treatment with lauric acid.

The tests demonstrate that lauric acid given orally at a continuous rate of 1 gram per kilogram of body weight per day is effective in the treatment of paratuberculosis in cows.

I claim:

1. A method for treating diseases caused by Mycobacterium species selected from the group consisting of M. tuberculosis and M. paratuberculosis in mammals which comprises orally administering to mammals in need of said treatment, at regular intervals, an effective dose of lauric acid.

2. A method for treating mammals suffering from diseases caused by Mycobacterium species selected from the group consisting of M. tuberculosis and M. paratuberculosis which comprises orally administering to said mammals an effective dose of lauric acid.

3. A method for treating mammals suffering from diseases caused by Mycobacterium species selected from the group consisting of M. tuberculosis and M. paratuberculosis comprising orally administering to said mammals an effective dose, as a food stuff, comprising about 4% to 8% lauric acid by weight of the daily food consumption of said mammal.

4. A method for treating mammals suffering from diseases caused by Mycobacterium species selected from the group consisting of M. tuberculosis and M. paratuberculosis comprising orally administering to said mammals an effective dose, as a liquid preparation, comprising about 20% to 90% lauric acid by weight of the liquid preparation.

* * * * *

UNITED STATES PATENT AND TRADEMARK OFFICE
CERTIFICATE OF CORRECTION

PATENT NO. : 4,223,040
DATED : September 16, 1980
INVENTOR(S) : John M. Carroll

It is certified that error appears in the above—identified patent and that said Letters Patent is hereby corrected as shown below:

Col. 2, lines 32-33, "particularity" should read --practicality--;

Col. 3, line 61, "fice" should read --five--;

Col. 6, Table 1, in the heading "INFECETED" should read -- INFECTED --.

Col. 7, line 2, "INFECETED" should read -- INFECTED --;

Signed and Sealed this

Twenty-fourth Day of March 1981

[SEAL]

Attest:

RENE D. TEGTMEYER

Attesting Officer     Acting Commissioner of Patents and Trademarks